(12) United States Patent
Styrc

(10) Patent No.: US 9,883,959 B2
(45) Date of Patent: Feb. 6, 2018

(54) DEVICE FOR TREATING A BLOOD CIRCULATION CONDUIT

(71) Applicant: CORMOVE, Ivry-le-Temple (FR)

(72) Inventor: Witold Styrc, Kopstal (LU)

(73) Assignee: Cormove, Ivry-le-Temple (FR)

( * ) Notice: Subject to any disclaimer, the term of this patent is extended or adjusted under 35 U.S.C. 154(b) by 215 days.

(21) Appl. No.: 14/434,990

(22) PCT Filed: Oct. 1, 2013

(86) PCT No.: PCT/EP2013/070404
§ 371 (c)(1),
(2) Date: Apr. 10, 2015

(87) PCT Pub. No.: WO2014/056754
PCT Pub. Date: Apr. 17, 2014

(65) Prior Publication Data
US 2015/0265442 A1    Sep. 24, 2015

(30) Foreign Application Priority Data

Oct. 12, 2012  (FR) ...................... 12 59782

(51) Int. Cl.
*A61F 2/95*   (2013.01)
*A61F 2/24*   (2006.01)
*A61F 2/962*  (2013.01)

(52) U.S. Cl.
CPC ............. *A61F 2/95* (2013.01); *A61F 2/2436* (2013.01); *A61F 2/962* (2013.01); *A61F 2002/9517* (2013.01); *A61F 2002/9522* (2013.01)

(58) Field of Classification Search
CPC .......... A61F 2/95; A61F 2/2436; A61F 2/962; A61F 2002/9522; A61F 2002/9517
See application file for complete search history.

(56) References Cited

U.S. PATENT DOCUMENTS 7,780,725 B2 *  8/2010  Haug ................... A61F 2/2418
                                                 623/2.17
7,935,144 B2 *  5/2011  Robin .................. A61F 2/2418
                                                 623/2.1
9,314,355 B2    4/2016  Styrc et al.
(Continued)

FOREIGN PATENT DOCUMENTS

FR            2863160       6/2005
FR            2 945 440    11/2010
WO        WO 2008/138584   11/2008

*Primary Examiner* — Julian W Woo
(74) *Attorney, Agent, or Firm* — Davidson, Davidson & Kappel, LLC

(57) ABSTRACT

A device (10) for treating a blood circulation conduit is provided. The device (10) includes an implant (20) intended to be placed in the conduit (3). The implant includes a tubular endoprosthesis (22) and an insertion member (24). The device (10) includes a tool (26) for deploying the implant (20), able to occupy a configuration for introducing the implant (20) into the conduit. It includes an actuation member (28) of the insertion member (24), able to be actuated from a proximal end (85A) of the deploying tool (26) in order to have the insertion member (24) pass from an inactive position to an active position. The insertion member (24) is freely movable with respect to the endoprosthesis (22) between its inactive position and its active position.

11 Claims, 3 Drawing Sheets

(56) References Cited

U.S. PATENT DOCUMENTS

| | | |
|---|---|---|
| 2005/0283231 A1 | 12/2005 | Haug et al. |
| 2011/0251681 A1 | 10/2011 | Shipley et al. |
| 2011/0301702 A1 | 12/2011 | Rust et al. |
| 2017/0035562 A1* | 2/2017 | Quadri .................. A61F 2/2418 |

* cited by examiner

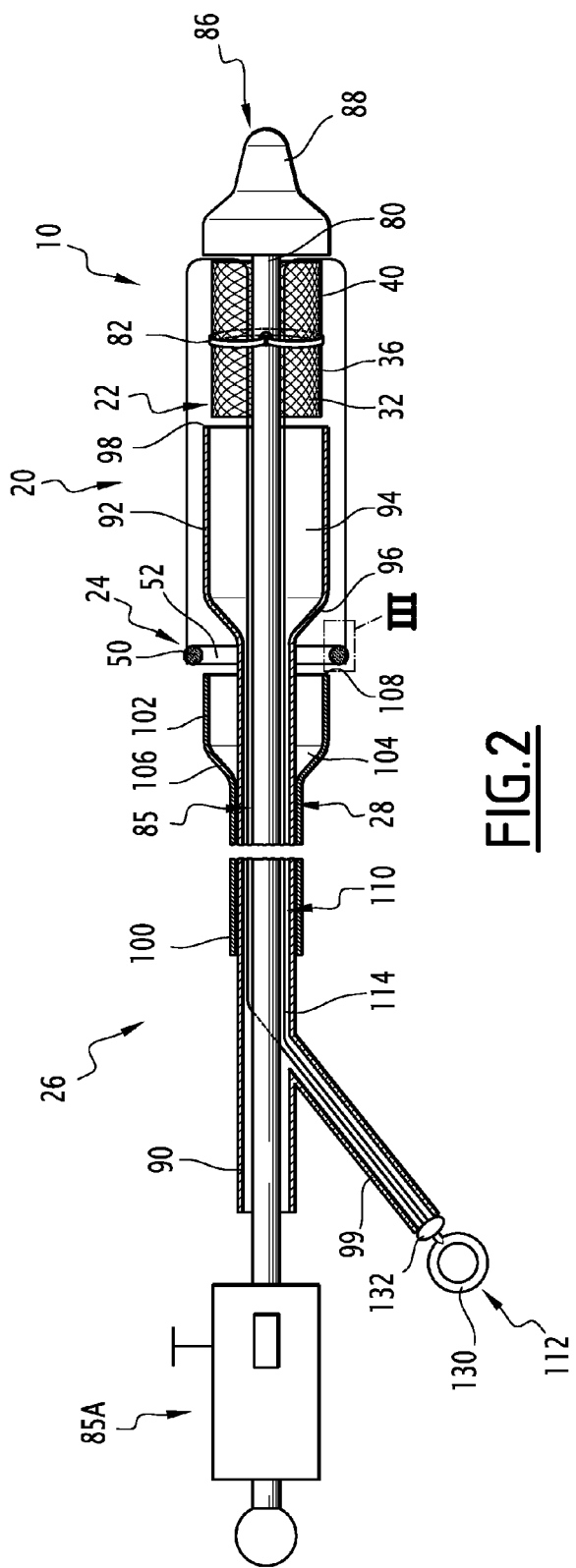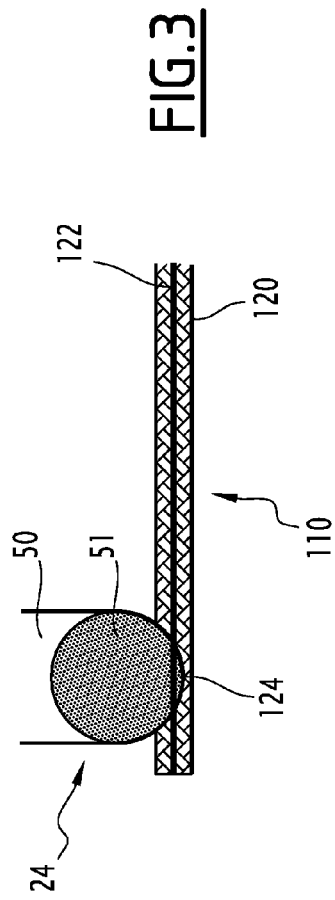

DEVICE FOR TREATING A BLOOD CIRCULATION CONDUIT

The present disclosure relates to a device for treating a blood circulation conduit, comprising:

an implant intended to be placed in the conduit, the implant comprising:

a tubular endoprosthesis with an axis X-X' having a frame which may be deployed radially between a contracted state and an expanded state;

at least one more flexible insert member than the frame, the insert member being movable between an inactive position positioned axially away from the endoprosthesis and an active insertion position, in which it is intended to be interposed between an outer surface of the endoprosthesis and the conduit, a tool for deploying the implant, able to occupy a configuration for introducing the implant into the conduit, in which the tool maintains the frame in its contracted state, and a configuration for releasing the implant, in which the frame occupies its expanded state;

at least one member for actuating the insertion member, which may be actuated from a proximal end of the deploying tool in order to have the insert member pass from its inactive position to its active position.

This device is notably applied to treating defective valves, like heart valves or lung valves.

BACKGROUND

The heart includes valves which are present at the outlet of the right ventricle (pulmonary or tricuspid valve) and of the left ventricle (aortic or mitral valve).

These valves ensure one way circulation of blood flow, avoiding blood backflow at the end of the ventricle contraction.

However, diseases or deformities affect proper operation of the valves.

In particular, the latter may suffer from calcification thus allowing backflow or regurgitation towards the ventricle at the auricle having expelled the blood flow. The regurgitation problem leads to abnormal expansion of the ventricle which finally produces heart failure.

In order to treat this type of disease in a surgical way the implantation of an endovalve between the leaflets of the affected native valve is known. This endovalve comprises a tubular endoprosthesis formed by a self-expandable trellis and a flexible obturator or valve most often made in a tissue of animal origin. The flexible obturator is permanently fixed in the endoprosthesis.

Such endovalves are implantable via an endoluminal route, which considerably limits the risks associated with implantation of the valve, notably in terms of mortality.

In certain cases, the endovalves do not give entire satisfaction after their implantation. Indeed, although the outer surface of the endoprosthesis is spontaneously applied against the seat of the native valve, by flattening the leaflets between the seat and the outer surface of the endoprosthesis, leaks may subsist around the outer surface of the endoprosthesis, notably at the joints defined between the leaflets of the native valve. These leaks occur in more than 50% of the patients having been subject to such an operation.

In order to overcome this problem, US 2005/0283231 describes an implant comprising an endoprosthesis and a prosthetic valve fixed in the endoprosthesis. The leaflets of the prosthetic valve are extended with foldable segments around the endoprosthesis so as to be interposed between the wall of the conduit and the outer surface of the endoprosthesis. These folded segments around the endoprosthesis are able to fill at least partly the leaks which may occur around the implant.

However, each folded segment is bound to the valve. It is therefore difficult to position it with accuracy, in particular with respect to the endoprosthesis and/or to the blood flow conduit in which the implant is positioned. In particular, the position at which the folded segment has to be positioned in the native valve is difficult to determine for ensuring a good seal around the endoprosthesis.

SUMMARY OF THE INVENTION

It is an object of the present invention to provide a treatment device comprising an implant which may be sealably positioned in a blood flow conduit, the seal being easily made and being able to be adapted to the anatomic configuration of the patient.

The present invention provides a device of the aforementioned type, characterized in that the insertion member is freely movable with respect to the endoprosthesis between its inactive position and its active position.

The device according to the invention may comprise one or more of the following characteristics, taken individually or according to all the technically possible combinations:

the actuation member is fixed so as to be releasable on the insertion member;

the actuation member includes a thread-like line extending between the insertion member and a proximal end of the deploying tool;

the thread-like line includes a flexible slender member, and a rigid pin which may be moved in the slender member;

the slender member delimits a housing for receiving the insertion member, the pin being mounted so as to be movable in the housing between a position for fixing the insertion member and a position for releasing the insertion member;

the deploying tool includes a capsule for receiving the endoprosthesis, able to maintain the endoprosthesis in its contracted state, and an auxiliary capsule for receiving the insertion member, axially shifted with respect to the receiving capsule;

the deploying tool includes a support for axially supporting and maintaining the endoprosthesis on the deploying tool and at least one thread like link for retaining the frame in its contracted state against the support, the link being able to be actuated between a configuration for maintaining the frame in its contracted state and a configuration for releasing the frame in which the frame occupies its expanded state, the actuation member being positioned outside the support;

the actuation member comprises at least one proximal segment inserted through the endoprosthesis, and a distal segment connected to the proximal segment and rolled up outside the endoprosthesis;

in the configuration for introducing the implant into the conduit, the insertion member is positioned in a proximal way with respect to the endoprosthesis;

the insertion member comprises a ring-shaped cushion;

the insertion member includes a radio-opaque material.

The present invention also provides a method for treating a blood circulation conduit comprising the following steps:

providing a device as defined above, the deploying tool occupying a configuration for introducing the implant, the frame occupying its contracted state, the insertion member being positioned in its inactive position;

freely moving the insertion member by actuating the actuation member from its inactive position to its active position so as to place it facing the endoprosthesis;

deploying the endoprosthesis from its contracted state to its expanded state so as to bear against the insertion member.

BRIEF DESCRIPTION OF THE DRAWINGS

The invention will be better understood upon reading the description which follows, only given as an example, and made with reference to the appended drawings, wherein:

FIG. 2 is a view similar to FIG. 1 during a first step for deploying the implant contained in the device;

FIG. 3 is a detail marked as III in FIG. 2;

DETAILED DESCRIPTION

FIGS. 1 to 5 illustrate a first treatment device 10 according to an embodiment of the invention. This device 10 is notably intended for implanting an endovalve comprising a tubular endoprosthesis and a valve, as a replacement for a native heart valve 12, visible in FIGS. 4 and 5.

Figure 4:
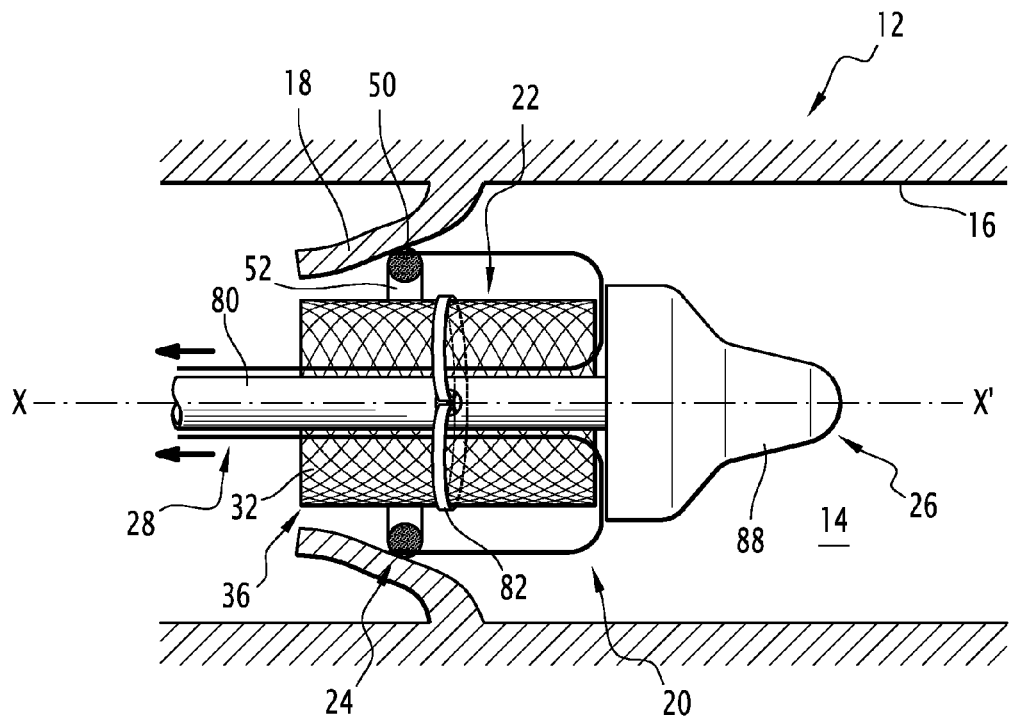
FIG. 4 is a view of the distal end of the device of FIG. 2, in a subsequent deployment step.
Figure 5:
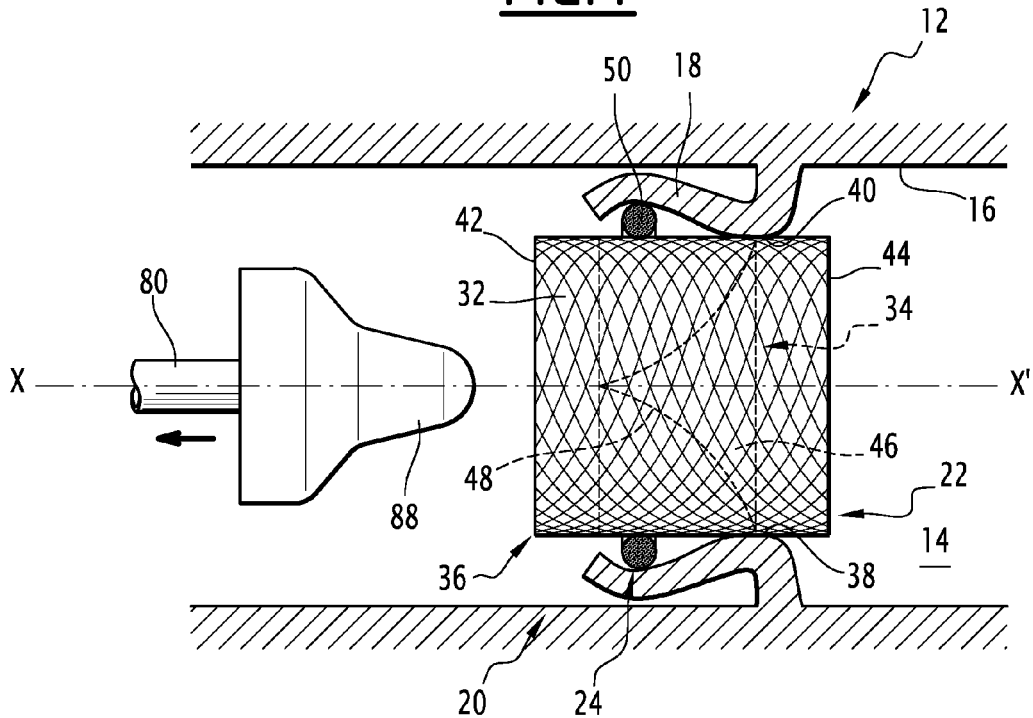
FIG. 5 is a view of the implant taken once the deployment is finished.

As illustrated in FIGS. 4 and 5, the native valve 12 is located in a blood conduit 14 delimited inside a peripheral wall 16. The native valve 12 comprises a plurality of movable native leaflets 18 in the conduit 14 from the wall 16.

As illustrated by FIGS. 1 to 5, the device 10 comprises an implant 20 which includes an endoprosthesis 22 and an insertion member 24, freely mounted so as to be movable with respect to the endoprosthesis 22, in order to ensure the seal around the endoprosthesis 22. The device 10 further comprises a tool 26 for deploying the endoprosthesis, and at least one actuation member 28 of the insertion member 24 in order to move it between an inactive position for introduction into the conduit 14, and an active position for interposition around the endoprosthesis 22, upon deploying the implant 20.

As illustrated by FIG. 5, the endoprosthesis 22 advantageously forms an endovalve. It has a tubular shape with an axis X-X' and delimits a central passage 32 for circulation of the blood axially opening on either side of the endoprosthesis 22. The endoprosthesis 22 bears a valve 34 or obturator added onto the endoprosthesis 22 inside the passage 32.

The endoprosthesis 22 is formed with a tubular openworked frame 36 comprising a trellis of wires which have spring properties. The frame 36 is obtained by braiding at least one wire of stainless steel, of a shape memory alloy, or of a polymer. Alternatively, the frame 36 is obtained by cutting a tube, for example by means of a laser.

With reference to FIG. 5, the frame 36 defines an inner peripheral surface 38 and an outer peripheral surface 40. The surfaces 38 and 40 are substantially cylindrical and extend around the axis X-X' between a proximal peripheral edge 42, located on the left in FIG. 5 and a distal peripheral edge 44, located on the right in FIG. 5.

The inner surface 38 interiorly defines the central passage 32. The outer surface 40 is intended to be at least partly applied against the wall 16 and/or against the leaflets 18, as this will be seen below.

The endoprosthesis 22 may be deployed between a contracted state, in which it has a small diameter, with view to its introduction into the conduit 14, and an expanded state, forming its rest state, in which it has a large diameter. In the example illustrated in FIGS. 1 to 4, the endoprosthesis 22 may be spontaneously deployed between its contracted state and its expanded state. It is thus self-expandable.

The valve 34 is for example made on the basis of a native valve from an animal like a pig. Alternatively, it is made on the basis of natural tissues such as bovine, porcine or ovine pericardium, or on the basis of synthetic tissues.

Conventionally, the valve 34 comprises a tubular base 46 fixed on the inner surface 38 of the frame 36, and several flexible leaflets 48 for obturating the central passage 32 which extend the base 46 downwards.

The leaflets 48 may be moved radially towards the axis X-X' of the passage 38 between an obturation position, in which they substantially totally prevent passing of the blood through the passage 32, and a position for clearing the passage 32 in which they are substantially flattened against the inner surface 38 and they let the blood pass through the passage 32.

In the obturation position, the leaflets 48 have a convergent section towards the proximal edge 42 of the valve.

In the example illustrated in FIGS. 1 to 5, the insertion member 24 is ring shaped. It comprises an annular seal cushion 50 intended to be interposed between the outer surface 40 of the endoprosthesis 22 and the wall 16 of the conduit 14.

The cushion 50 is for example made on the basis of a foam, such as a foam of expansed silicone or on the basis of a fabric. It extends over the whole periphery around the axis X-X'. It has a length, taken along the axis X-X', of less than that of the endoprosthesis 22, taken along the axis X-X' between its proximal edge 42 and its distal edge 40.

The cushion 50 comprises at least one radio-opaque material 51 able to be observed by radiography through the skin of the patient.

The insertion member 24 delimits a central lumen 52 of axis X-X' and with a transverse extent greater than the width of the cushion 50.

The insertion member 24 is able to be radially contracted so as to be positioned in the deploying tool 26, when the deploying tool 26 occupies a configuration for introducing the implant 20 into the conduit 14.

The insertion member 24 is able to be spontaneously deployed to an expanded configuration once it is extracted out of the tool 26, in which the transverse extent of the central lumen 52 is greater than the maximum transverse extent of the endoprosthesis 22 in the contracted state and is less than or substantially equal to the maximum transverse extent of the endoprosthesis 22 in its expanded state.

As specified above, the insertion member 24 may be freely moved with respect to the endoprosthesis 22. As such, it is not connected to the endoprosthesis 22 or to the valve 34. Thus, the insertion member 24 may be freely moved along the endoprosthesis 22, when the latter occupies its retracted state, in order to occupy any axial position along the length of the endoprosthesis 22.

Figure 1:
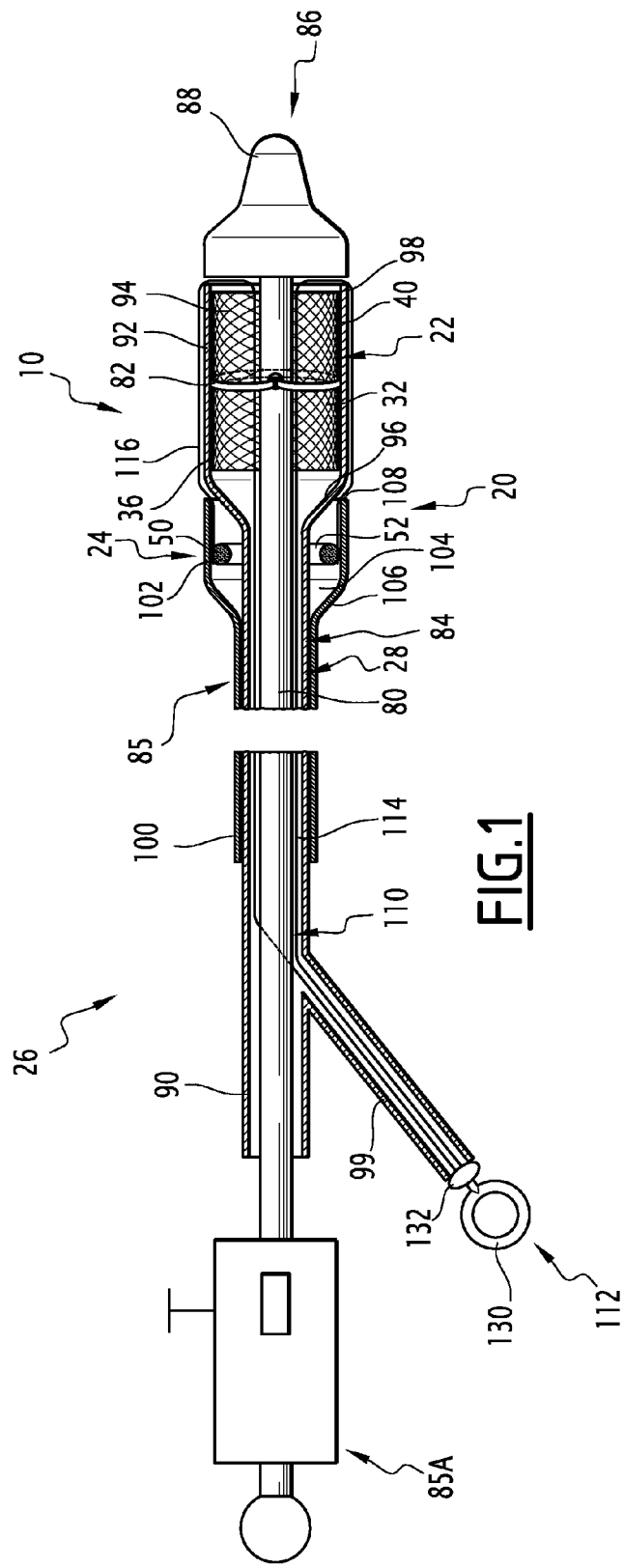
FIG. 1 is a schematic view as a partial section, of a first treatment device according to an embodiment of the invention, in an initial configuration for implantation in a blood conduit.

Further, in the inactive position, for example illustrated in FIG. 1, the insertion member 24 is totally positioned axially away from the endoprosthesis 22 without being connected to the latter.

In the active position, the insertion member 24 has been moved so as to be placed facing the outer surface 40 of the endoprosthesis 22, in an axial position selected with respect to the endoprosthesis 22 or/and to the wall 16 of the conduit 14 or/and to the position of the leaflets 18.

Thus, the relative position of the insertion member 24 with respect to the wall 16 of the conduit 14 and to the leaflets 18, and with respect to the endoprosthesis 22, may be adjusted in a totally free way by the user of the device, depending on the anatomic conformation of the conduit 14 in which the implant 20 has to be positioned.

In the example illustrated by FIG. 1, the deploying tool 26 comprises a support 80 for axially supporting and maintaining the endovalve 22 in the conduit 14, advantageously at least one thread-like link 82 for maintaining the frame 36 in its contracted state against the support 80, and an inner protective sheath 84 able to interiorly receive the implant 20 and the support 80. The tool 26 further preferably includes an outer sheath 85 for maintaining the insertion member 24 in its contracted configuration.

The deploying tool 26 is for example of the type described in French application FR-A-2 863 160 of the applicant, which is published as U.S. Publication No. 2005/0119722, hereby incorporated by reference herein.

The tool 26 and its support 80 extend between a proximal end 85A, intended to be handled by a surgeon outside the human body, and a distal end 86 intended to be introduced into the conduit 14 as far as the valve 12.

At the distal end 86, the support 80 is provided with a profile nose 88 with view to introducing without any damage via the endoluminal route the deploying tool 26 containing the implant 20, into the conduit 14.

As this will be seen later on, the tool 26 is able to be handled so as to have it pass from a configuration for introducing the implant 20 into the conduit 14, to a configuration for releasing the implant 20 in the conduit 14.

In the introduction configuration, the endoprosthesis 22 is coaxially mounted around the support 80, under the nose 88 in the vicinity of the distal end 86 in the inner sheath 84. The support 80 is thus inserted into the central passage 32 and through the insertion member 24.

The insertion member 24 is positioned in its inactive position, in a proximal way with respect to the endoprosthesis 22 around the inner sheath 84, out of the latter. The endoprosthesis 22 is thus axially positioned between the nose 88 and the insertion member 24.

The thread-like link 82 is a releasable link. It encircles the frame 36 of the endoprosthesis 30 between its distal edge 44 and its proximal edge 42.

The link 82 may be actuated and released from the proximal end of the tool 24. It is able to be maneuvered between a configuration for maintaining the frame 36 in its contracted state against the support 80, and a configuration for releasing the frame 36 in which the frame 36 occupies its expanded state.

The main sheath 84 is coaxially mounted around the support 80 and the endoprosthesis 20.

It includes a proximal hollow rod 90 and a flared distal capsule 92, with a diameter greater than that of the rod 90. The capsule 92 interiorly defines a cylindrical housing 94 for receiving the endoprosthesis 22.

The capsule 92 extends between a proximal shoulder 96 which it forms with the rod 90 and a circumferential distal edge 98 intended to be placed bearing against the nose 88.

The inner sheath 84 has, in the vicinity of its proximal end, a passage bypass 99 of each actuation member 28. The passage bypass 99 opens inside the sheath 84.

The sheath 84 may be moved axially along the axis X-X' around the support 80 between a distal position illustrated in FIG. 1, which it occupies in the introduction configuration, an intermediate position illustrated in FIG. 2, and a proximal withdrawal position (not shown) which it occupies in the configuration for releasing the implant 20.

In the distal position visible in FIG. 1, the distal edge 98 of the sheath 84 is flattened against the nose 88. The capsule 92 extends facing the endoprosthesis 22 and maintains it in its contracted state. The housing 94 is distally obturated by the nose 88.

In the intermediate position visible in FIG. 2, the sheath 84 has been partly moved towards the proximal end of the support 80 so as to discover the endoprosthesis 22 upon moving away from the nose 88. The distal edge 98 is then placed between the endoprosthesis 22 and the insertion member 24.

In the proximal position, the endoprosthesis 22 is entirely uncovered and the sheath 84 has been extracted out of the patient.

The outer sheath 85 is coaxially mounted around the inner sheath 84, in a proximal way with respect to the latter. In a similar way to the inner sheath 84, it includes a proximal hollow rod 100 and a flared distal auxiliary capsule 102 with a diameter greater than that of the hollow rod 100.

The auxiliary capsule 102 interiorly defines an auxiliary housing 104 for receiving the insertion member 24.

The auxiliary capsule 104 extends between a proximal shoulder 106 formed with the rod 100 and a circumferential distal edge 108 intended to be placed bearing against the main capsule 92.

Like the outer sheath 84, the inner sheath 85 may be moved axially along the axis X-X' around the main sheath 84 between a distal position illustrated in FIG. 1, which it occupies in the introduction configuration, an intermediate position illustrated in FIG. 2, and a proximal withdrawal position (not shown) which it occupies in the configuration for releasing the implant 20.

In the distal position visible in FIG. 1, the distal edge 108 of the inner sheath 85 is applied against the main sheath 84, advantageously at the shoulder 96.

The auxiliary capsule 102 then extends facing the insertion member 24 and maintains this member 24 in its contracted configuration.

The auxiliary housing 104 is distally obturated by the capsule 92.

In the intermediate position visible in FIG. 2, the outer sheath 85 has been moved towards the proximal end 85A of the deploying tool 26, by sliding on the inner sheath 84, in order to expose the insertion member 24.

The auxiliary capsule 102 is then positioned in a proximal way with respect to the insertion member 24 and with respect to the main capsule 92.

A free ring shaped space therefore extends between the capsules 92 and 102, allowing deployment of the insertion member 24 towards its deployed configuration. The distal edge 108 is then placed in a proximal way with respect to the insertion member 24.

In the proximal position, the implant 20 has been totally extracted and the auxiliary sheath 85 has been extracted out of the patient.

As illustrated in FIG. 2, the device 10 includes at least one actuation member 28, advantageously two actuation members 28. Each actuation member 28 has a distal end connected to the insertion member 24.

Each actuation member 28 includes a flexible thread like line 110 connected to a handling member 112 located at its proximal end.

Each thread like line 110 extends through the inner sheath 84.

In the example illustrated in FIG. 1, the line 110 comprises a proximal segment 114 inserted into the inner sheath 84 and a distal segment 116 protruding out of the sheath 84 and folded around the sheath 84 so as to be connected to the insertion member 24.

The proximal segment 114 is attached to the handling member 112. It successively extends through the bypass 99, through the hollow rod 90, and then through the main capsule 92. It is positioned in the central passage 32 of the endoprosthesis 22.

The distal segment 116 is rolled up around the distal edge 98 of the main capsule 92. It extends outwards and along the capsule 92 as far as the insertion member 24. It is removably attached on the insertion member 24.

As illustrated by FIG. 3, the link 110 includes a flexible slender member 120 and rigid pin 122 mounted through the slender member 120.

The slender member 120 is for example formed by a braid made on the basis of at least one weaving thread.

The slender member 120 delimits, in the vicinity of its distal end, a housing 124 for receiving the insertion member 24.

The rigid pin 122 is for example formed on the basis of a solid metal rod for example in a flexible metal such as Nitinol, or in Nylon.

The pin 122 is able to cross the receiving housing 124 in order to retain the insertion member 24. For this purpose, the pin 122 is movable with respect to the slender member 120 between a position for fixing the insertion member 24, in which it crosses the housing 124, and a position for releasing the insertion member 24, in which it has been retracted towards the proximal end of the tool 24 so as to be extracted out of the housing 124.

In this example, the handling member 112 is common to all the actuation members 28. It protrudes out of the sheath 84 from the bypass.

In the example illustrated in FIG. 2, the member 112 includes a gripping member 130, advantageously ring-shaped, and a member 132 for releasing the pin 122 with respect to the slender member 120.

The release member 132 is able to be actuated by a user of the device for releasing the pin 122 and for moving it from its attachment position to its release position.

As this will be seen below, the handling member 112 is able to be extracted in a proximal way out of the tool 24 for axially moving the insertion member 24 with respect to the endoprosthesis 22.

In the intermediate configuration of FIG. 2, when an increasing length of the actuation member 28 is extracted out of the sheath 84 through the passage 99, the length of the proximal segment 114 increases, and the length of the distal segment 116 decreases correspondingly. The insertion member 24 then moves towards the distal end 86 of the tool 24 so as to be placed facing the outer surface 40 of the endoprosthesis 22.

The operation of the treatment device 10 according to an embodiment of the invention, during the implantation of an implant 20 in a native valve 12 will now be described.

Initially, the implant 20 is mounted in the deploying tool 26. For this purpose, the endoprosthesis 22 is coaxially engaged onto the support 80.

Each actuation member 28 is introduced into the inner sheath 84 and is engaged through the central passage 32 of the endoprosthesis 22. Next, it is extracted out of the sheath 84 and rolled up around the sheath 84 so as to be placed facing and outside the rod 80. The insertion member 24 is engaged around the inner sheath 84 between the inner sheath 84 and the outer sheath 85.

The pin 122 is then passed into its release position and the insertion member 24 is introduced into the housing 124. Next, each pin 122 is introduced through the insertion member 24 in order to immobilize it with respect to the actuation member 28 and passing into its attachment position.

Next, the insertion member 24 is placed in its retracted configuration. The auxiliary capsule 102 is positioned around the insertion member 24 for maintaining it in this configuration.

The thread like link 82 is engaged around the endoprosthesis 22 and is actuated so as to have the frame 36 pass from its expanded state with a large diameter to its contracted state against the support 80, with a small diameter.

The inner sheath 84 then occupies its distal position, bearing against the nose 88. The outer sheath 85 also occupies its distal position bearing upon the inner sheath 84.

The deploying tool 26 then occupies its configuration for introduction into the conduit 14, illustrated in FIG. 1, in which it has a minimum radial size. In this configuration, the insertion member 24 is shifted away from the outer surface 40 of the endoprosthesis 22. Further, the insertion member 24 is maintained in a contracted configuration with respect to the auxiliary capsule 102.

Next, the tool 26 is introduced into the blood conduit 14 via an endoluminal route.

The distal end 86 of the tool 24 is moved towards the valve 12, until the endoprosthesis 22 is placed between the leaflets 18 of the native valve 12 by moving them away radially via the sheath 84.

The support 80 is then maintained fixed in position. The inner sheath 84 is then drawn towards its intermediate position for exposing the endoprosthesis 22. For this purpose, it is moved in a proximal way with respect to the support 80, so that the distal edge 98 moves away from the nose 88 and is placed in a proximal way with respect to the proximal edge 42 of the endoprosthesis 22.

Next, the outer sheath 85 is moved towards its intermediate position. The outer sheath 85 slides along the inner sheath 84 in a proximal way in order to expose the insertion member 24. This movement is performed until the distal edge 108 of the auxiliary capsule 102 is located in a proximal way with respect to the insertion member 24.

As illustrated by FIG. 2, the insertion member 24 is then deployed radially towards its deployed configuration.

Subsequently, the user takes hold of the handling member 122 located at the end of each actuation member 28. He/she extracts an increasing length of each actuation member 28 in order to axially move the insertion member 24 towards the distal end 86 of the tool 24.

The insertion member 24 is then displaced between the leaflets 18 of the native valve 12 and is placed facing the outer surface 40 of the endoprosthesis 22, at a distance from the latter.

Next, the operator deploys the endoprosthesis 22.

In the example illustrated in the figures, the operator releases the thread like link 82 in order to cause radial expansion of the frame 36.

During this deployment, the frame 36 passes into an expanded state and the tool then occupies a release configuration.

The outer surface 40 of the frame 36 is flattened against the wall 16 of the conduit 18 by crushing the leaflets 18, with interposition of the insertion member 24.

Thus, the insertion member 24 is blocked between the wall 16 of the conduit 14 and the outer surface 40 of the endoprosthesis 22, notably at the native leaflets 18, and obturates the ring shaped space located around the outer surface 40. Thus, the cushion 50 is placed in the free spaces between the native leaflets 18, which sealably obturates the conduit 14 around the endoprosthesis 22.

During diastole, the blood which would tend to move up in the conduit 14, obturates the leaflets 48 of the valve 34 borne by the endoprosthesis 22. Further, the blood cannot pass around the endoprosthesis 22, the presence of the insertion member which obturates the ring shaped space 24 located around the endoprosthesis 22 being taken into account.

The risk of a leak through the endoprosthesis 22 and around the latter is therefore substantially reduced during diastole.

The pin 122 is released for having it pass into its released position by action on the release member 132. Each actuation member 28 is then free to move with respect to the insertion member 24 and is extracted by traction out of the conduit 24.

The support 80 is then extracted out of the body of the patient by having the nose 88 pass through the central passage 32.

The device 10 is therefore particularly simple to use. The insertion member 24 being totally free with respect to the endoprosthesis 22, its axial positioning may be achieved very accurately with respect to the endoprosthesis 22, and with respect to the wall 16 of the conduit 14, in order to ensure an optimum seal around the endoprosthesis 22.

What is claimed is:

1. A device for treating a blood conduit comprising:
   an implant configured for placing in the conduit, the implant comprising:
      a tubular endoprosthesis of an axis having a frame which may be radially deployed between a contracted state and an expanded state; and
      at least one ring-shaped inserter which is more flexible than the frame, the inserter being movable between an inactive position positioned axially away from the endoprosthesis and an active insertion position, in which it is configured to be interposed between an outer surface of the endoprosthesis and the conduit;
   a deployer for deploying the implant, the deployer being adapted to occupy a configuration for introducing the implant into the conduit, in which the deployer maintains the frame in a contracted state of the frame, the deployer being adapted to occupy a configuration for releasing the implant, in which the frame occupies an expanded state of the frame;
   at least one actuator of the inserter, the actuator being configured to be actuated from a proximal end of the deployer in order to have the inserter pass from an inactive position to an active position of the inserter;
   the inserter being freely movable with respect to the endoprosthesis between the inactive position and the active position.

2. The device according to claim 1 wherein the actuator is releasably attached onto the inserter.

3. The device according to claim 1 wherein the actuator includes a thread shaped line extending between the inserter and a proximal end of the deployer.

4. The device according to claim 3 wherein the thread shaped line includes a flexible slender member, and a rigid pin which may be moved in the slender member.

5. The device according to claim 4 wherein the slender member delimits a housing for receiving the inserter, the pin being mounted so as to be movable in the housing between an attachment position of the inserter, and a position for releasing the inserter.

6. The device according to claim 1 wherein the deployer includes a capsule for receiving the endoprosthesis, the capsule being configured to maintain the endoprosthesis in the contracted state, the deployer including an auxiliary capsule for receiving the inserter, the auxiliary capsule being axially shifted with respect to the receiving capsule.

7. The device according to claim 1 wherein the deployer includes a support for axially supporting and maintaining the endoprosthesis on the deployer and at least one thread shaped link for retaining the frame in the contracted state against the support, the link configured for being actuated between a configuration for maintaining the frame in the contracted state and a configuration for releasing the frame in which the frame occupies the expanded state, the actuator being positioned outside the support.

8. The device according to claim 1 wherein the actuator comprises at least one proximal segment inserted through the endoprosthesis, and a distal segment connected to the proximal segment and rolled up outside the endoprosthesis.

9. The device according to claim 1 wherein in the configuration for introducing the implant into the conduit, the inserter is positioned in a proximal way with respect to the endoprosthesis.

10. The device according to claim 1 wherein the inserter comprises a cushion.

11. The device according to claim 1 where in the inserter includes a radio-opaque material.

* * * * *